United States Patent [19]
Bellon et al.

[11] Patent Number: 6,162,909
[45] Date of Patent: *Dec. 19, 2000

[54] DEPROTECTION OF RNA

[75] Inventors: Laurent Bellon; Christopher T. Workman, both of Boulder, Colo.

[73] Assignee: Ribozyme Pharmaceuticals, Inc., Boulder, Colo.

[*] Notice: This patent is subject to a terminal disclaimer.

[21] Appl. No.: 09/326,154

[22] Filed: Jun. 4, 1999

Related U.S. Application Data

[63] Continuation of application No. 09/164,964, Oct. 1, 1998, Pat. No. 6,054,576.
[60] Provisional application No. 60/061,321, Oct. 2, 1997.
[51] Int. Cl.[7] .............................. C12Q 1/68; C07H 21/04
[52] U.S. Cl. ........................ 536/25.31; 435/6; 435/91.1; 435/91.31; 536/23.1
[58] Field of Search .......................... 435/6, 91.31, 91.1; 536/23.1, 23.2, 24.5, 25.31

[56] References Cited

U.S. PATENT DOCUMENTS

| | | | |
|---|---|---|---|
| 4,987,071 | 1/1991 | Cech et al. | 435/91.31 |
| 5,334,711 | 8/1994 | Sproat et al. | 536/24.5 |
| 5,625,047 | 4/1997 | Been et al. | 536/23.1 |
| 5,631,359 | 5/1997 | Chowrira et al. | 536/24.5 |

FOREIGN PATENT DOCUMENTS

| | | |
|---|---|---|
| 0 360 257 | 3/1990 | European Pat. Off. . |
| 91/03162 | 3/1991 | WIPO . |
| 92/07065 | 9/1991 | WIPO . |
| 93/15187 | 8/1993 | WIPO . |
| 95/23225 | 8/1995 | WIPO . |
| 96/19577 | 6/1996 | WIPO . |

OTHER PUBLICATIONS

Beigelman et al., "Chemical Modification of Hammerhead Ribozymes," *J. Biol. Chem.* 270:25702–25708 (1995).
Burgin et al., "Chemically Modified Hammerhead Ribozymes with Improved Catalytic Rates," *Biochemistry* 35:14090–14097 (1996) (vol. no mistakenly listed as 6).
Burke et al., "Structural Analysis and Modifications of the Hairpin Ribozyme," *Nucleic Acids and Molecular Biology*, edited by Eckstein and Lilley, Springer–Verlag Berlin Heidelberg, 10:129–143 (1996).
Cech et al., "Representation of the secondary and tertiary structure of group I introns," *nature structural biology* 1:273–280 (1994).
Cech, "Ribozymes and Their Medical Implications," *JAMA* 260:3030–3034 (1988).
Chrisoffersen and Marr, "Ribozymes as Human Therapeutic Agents," *J. Med. Chem.* 38:2023–2037 (1995).
Collins and Olive, "Reaction Conditions and Kinetics of Self–Cleavage of a Ribozyme Derived From Neurospora VS RNA," *Biochemistry* 32:2795–2799 (1993).
Forster and Altman, "External Guide Sequences for an RNA Enzyme," *Science* 249:783–786 (1990).

Gasparutto et al., "Chemical synthesis of a biologically active natural tRNA with its minor bases," *Nucleic Acids Research* 20(19):5159–5166 (1992).
Guerrier–Takada et al., "The RNA Moiety of Ribonuclease P Is the Catalytic Subunit of the Enzyme," *Cell* 35:849–857 (1983).
Guo and Collins, "Efficent trans–cleavage of a stem–loop RNA substrate by a ribozyme derived from Neurospora VS RNA," *EMBRO J.* 14:368–376 (1995).
Hampel and Tritz, "RNA Catalytic Properties of the Minimum (–)s TRSV Sequence," *Biochemistry* 28:4929–4933 (1989).
Hampel et al., "'Hairpin'Catalytic RNA Model: Evidence for Helices and Sequence Requirement for Substrate RNA," *Nucleic Acids Research* 18:299–304 (1990).
Haseloff and Gerlach, "Simple RNA Enzymes with New and Highly Specific Endoribonuclease Activities," *Nature* 334:585–591 (1988).
Hogrefe et al., "Effect of excess water on the desilylation of oligoribonucleotides using tetrabutylammonium floride," *Nucleic Acids Research* 21:4739–4741 (1993).
Jeffries and Symons, "A Catalytic 13–mer Ribozyme," *Nucleic Acids Research* 17:1371–1377 (1989).
Kim and Cech, "Three–dimensional model of the active site of the self–splicing rRNA precursor of Tetrahymena," *Proc. Natl. Acad. Sci. USA* 84:8788–8792 (1987).
Limbach et al., "Summary: the modified nucleosides of RNA," *Nucleic Acids Research* 22(12):2183–2196 (1994).
Pace and Smith, "Ribonuclease P: Function and Variation," *J. Biol. Chem.* 265:3587–3590 (1990).
Perreault et al., "Mixed Deoxyribo– and Ribo–Oligonucleotides with Catalytic Activity," *Nature* 344:565–567 (1990).
Perreault et al., "Relationship between 2'–Hydroxyls and Magensium Binding in the Hammerhead RNA Domain: A Model for Ribozyme Catalysis," *Biochemistry* 30:4020–4025 (1991).
Perotta and Been, "Cleavage of Oligoribonucleotides by a Ribozyme Derived from the Hepatitis δ Virus RNA Sequence," *Biochemistry* 31:16–21 (1992).
Pieken et al., "Kinetic Characterization of Ribonuclease–Resistant 2'–Modified Hammerhead Ribozymes," *Science* 253:314–317 (1991).
Pyle et al., "Building a Kinetic Framework for Group II Intron Ribozyme Activity: Quantitation of Interdomain Binding and Reaction Rate," *Biochemistry* 33:2716–2725 (1994).
Rossi et al., "Ribozymes as Anti–HIV –1 Therapeutic Agents: Principles Applications, and Problems," *Aids Research and Human Retroviruses* 8:138–189 (1992).
Saville and Collins, "A Site–Specific Self–Cleavage Reaction Performed by Novel RNA In Neurospora Mitochondria," *Cell* 61:685–696 (1990).

(List continued on next page.)

*Primary Examiner*—David Gozo
*Assistant Examiner*—Andrew Wang

[57] ABSTRACT

Method for one-pot deprotection of RNA molecules.

19 Claims, 5 Drawing Sheets

OTHER PUBLICATIONS

Seville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scaringe et al., "Chemical synthesis of biologically active oligoribonucleotides using —cyanoethyl protected ribonucleoside phosphoramidites," *Nucl Acids Res.* 18:5433–5441 (1990).

Slim and Gait, "Configurationally Defined Phosphorothioate–Containing Oligoribonucleotides in the study of the Mechanism of Cleavage of Hammerhead Ribozymes," *Nucleic Acids Research* 19:1183–1188 (1991).

Uhlenbeck, "A Small Catalytic Oligoribonucleotide," *Nature* 328:596–600 (1987).

Usman and Cedergren, "Exploiting the chemical synthesis of RNA," *TIBS* 17:334–339 (1992).

Usman and McSwiggen, "Ch. 30 —Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Usman etal., "Hammerhead ribozyme engineering," *Current Opinion in Structural Biology* 1:527–533(1996).

Vinayak et al., "Advances in the chemical synthesis and purification of RNA," *Nucleic Acids Symposium Series* 33:123–125 (1995).

Wincott et al., "Synthesis, deprotection, analysis and purification of RNA and ribozymes," *Nucleic Acids Research* 23:2677–2684 (1995).

Zaug et al., "The Tetrahymena Ribozyme Acts Like an RNA Restriction Endonuclease," *Nature* 324:429–433 (1986).

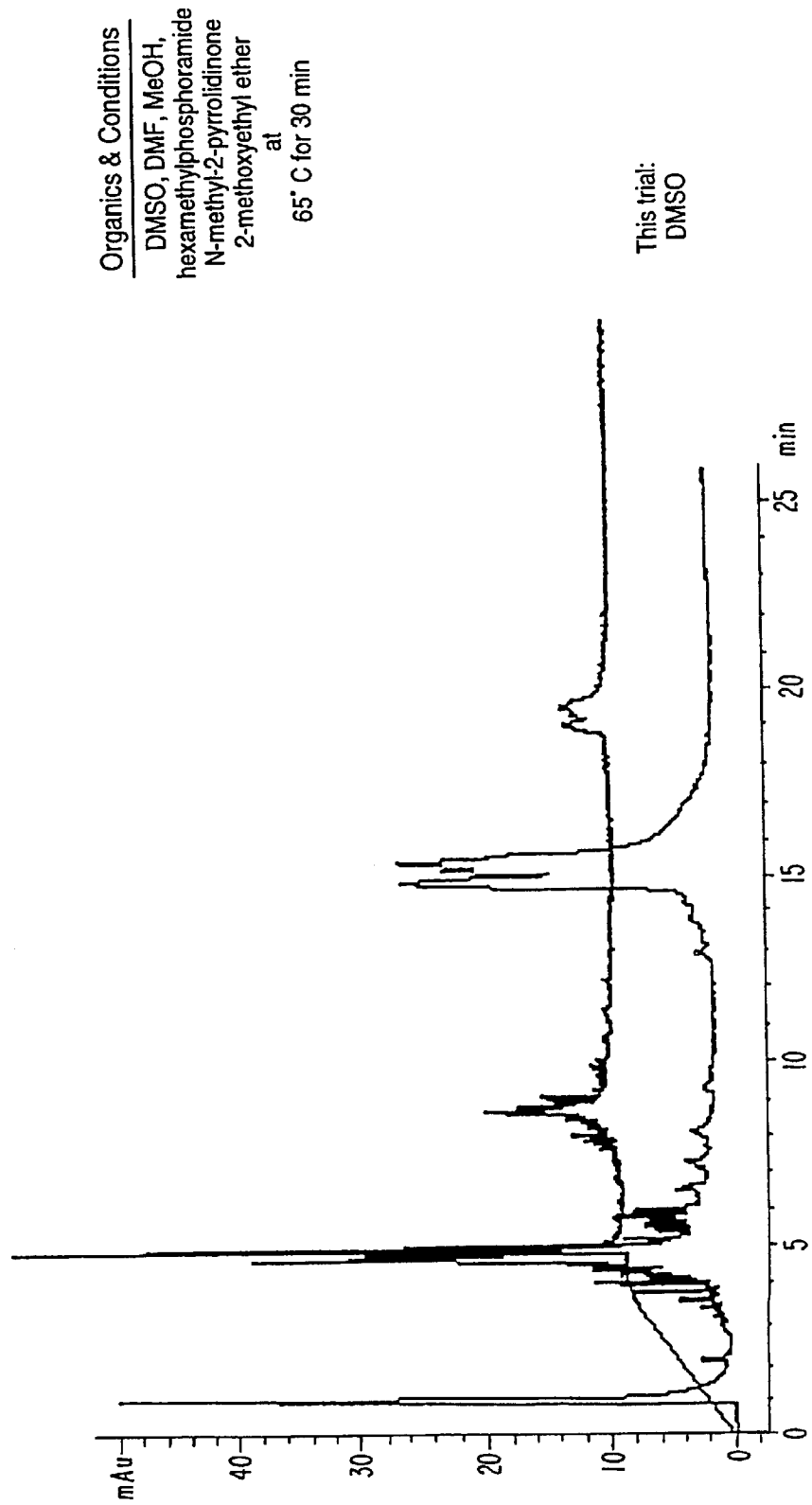

SEQUENCE LISTING

<160> NUMBER OF SEQ ID NOS: 4

<210> SEQ ID NO 1
<211> LENGTH: 17
<212> TYPE: RNA
<213> ORGANISM: Artificial Sequence
<220> FEATURE:
<223> OTHER INFORMATION: Synthesized nucleic acid molecule

<400> SEQUENCE: 1
uccucgcugg ggcuaag                                                  17

<210> SEQ ID NO 2
<211> LENGTH: 13
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, g, c or t.

<400> SEQUENCE: 2
cugangagcg aaa                                                      13

<210> SEQ ID NO 3
<211> LENGTH: 15
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.
    "y" stands for c or u.
    "h" stands for a, c or u.

<400> SEQUENCE: 3
nnnnnnnyng hynnn                                                    15

<210> SEQ ID NO 4
<211> LENGTH: 47
<212> TYPE: RNA
<213> ORGANISM: Artificial Sequence
<220> FEATURE:
<223> OTHER INFORMATION: Synthesized nucleic acid molecule
<220> FEATURE:
<223> OTHER INFORMATION: "n" stands for a, c, g or u.
    "h" stands for a, c or u.

<400> SEQUENCE: 4
nnnngaagnn nnnnnnnna aahannnnnn nacauuacnn nnnnnnn                  47

DEPROTECTION OF RNA

This Application is a continuation of Bellon et al., U.S. Ser. No. 09/164,964, filed Oct. 1, 1998, entitled "Deprotection of RNA", now U.S. Pat. No 6,054,576, which claimed the benefit of Bellon, et al., U.S. Provisional Application No. 60/061,321, entitled Deprotection of RNA", and filed Oct. 2, 1997. These applications are incorporated by reference herein including any drawings, tables and figures.

BACKGROUND OF THE INVENTION

This invention relates to the synthesis, deprotection, and purification of RNA.

Generally, RNA molecules are chemically synthesized and purified by methodologies based on the use of tetrazole to activate the RNA phosphoramidite, ethanolic-$NH_4OH$ to remove the exocyclic amino protecting groups, tetra-n-butylammonium fluoride (TBAF) to remove the 2'-OH alkylsilyl protecting groups, and gel purification and analysis of the deprotected RNA. Examples of chemical synthesis, deprotection, purification and analysis procedures for RNA are provided by Usman et al., 1987 *J. Am. Chem. Soc.,* 109, 7845; Scaringe et al. *Nucleic Acids Res.* 1990, 18, 5433–5341; Perreault et al. *Biochemistry* 1991, 30 4020–4025; Slim and Gait *Nucleic Acids Res.* 1991, 19, 1183–1188. All the above noted references are all hereby incorporated by reference herein.

The deprotection process commonly involves the deprotection of the exocyclic amino protecting groups by $NH_4OH$, which is time consuming (6–24 h) and inefficient. This step is then followed by treatment with TBAF to facilitate the removal of alkylsilyl protecting groups, which again is time consuming and not very effective in achieving efficient deprotection.

A recent modification of this two-step strategy for oligoribonucleotide deprotection has been reported by Wincott et al., (*Nucleic Acids Res.,* 1995, 23, 2677–2784) and by Vinayak et al., (*Nucleic Acids Symposium series,* 1995. 33, 123–125). The optimized conditions make use of aqueous methylamine at 65° C. for 15 minutes in place of the ammonium hydroxide cocktail to remove exocyclic amino protecting groups while the desilylation treatment needed to remove the 2'-OH alkylsilyl protecting groups utilizes a mixture of triethylamine trihydrogen fluoride (TEA.3HF), N-methyl-pyrrolidinone and triethylamine at 65° C. for 90 minutes, thereby replacing tetrabutyl ammonium fluoride.

Stinchcomb et al., International PCT Publication No. WO 95/23225 describe a process for one pot deprotection of RNA. On page 73, it states that:

"In an attempt to minimize the time required for deprotection and to simplify the process of deprotection of RNA synthesized on a large scale, applicant describes a one pot deprotection protocol . . . According to this protocol, anhydrous methylamine is used in place of aqueous methyl amine. Base deprotection is carried out at 65° C. for 15 minutes and the reaction is allowed to cool for 10 min. Deprotection of 2'-hydroxyl groups is then carried out in the same container for 90 minutes in a TEA.3HF reagent. The reaction is quenched with 16 mM TEAB solution."

SUMMARY OF THE INVENTION

This invention concerns a one-pot process for the deprotection of RNA molecules. This invention features a novel method for the removal of protecting groups from the nucleic acid base and 2'-OH groups, which accelerates the process for generating synthetic RNA in a high throughput manner (e.g., in a 96 well format).

Chemical synthesis of RNA is generally accomplished using a traditional column format on a RNA synthesizer where only one oligoribonucleotide is synthesized at a time. Simultaneous synthesis of more than one RNA molecule in a time efficient manner requires alternate methods to the traditional column format, such as synthesis in a 96 well plate format where up to 96 RNA molecules can be synthesized at the same time. To expedite this process of simultaneous synthesis of multiple RNA molecules, it is important to accelerate some of the time consuming processes such as the deprotection of RNA following synthesis (i.e. removal of base protecting group, such as the exocyclic amino protecting group and the phosphate protecting groups and the removal of 2'-OH protecting groups, such as the tButylDiMethylSilyl). In a preferred embodiment, the invention features a one-pot process for rapid deprotection of RNA.

Stinchcomb et al., supra described a one-pot protocol for RNA deprotection using anhydrous methylamine and triethylamine trihydrogen fluoride. This procedure involves the use of an anhydrous solution of base such as a 33% methylamine in absolute ethanol followed by neat triethylamine trihydrofluoride to effectively deprotect oligoribonucleotides in a one-pot fashion. However such a protocol may be cumbersome for deprotection of RNA synthesized on a plate format, such as a 96 well plate, because it may be necessary to separate the solid-support from the partially deprotected RNA prior to the 2'-hydroxyl deprotection. Also, since the methylamine solution used is anhydrous, it may be difficult to solubilize the negatively charged oligoribonucleotides obtained after basic treatment. So, in a first aspect the invention features the use of a 1:1 mixture of the ethanolic methylamine solution and a polar additive, such as dimethylsulfoxide (DMSO), N,N-dimethylformamide (DMF), methanol, hexamethylphosphoramide (HMPA), 1-methyl-2-pyrrolidinone (NMP), 2-methoxyethyl ether (glyme) or the like. More specifically, dimethylsufoxide is used to partially deprotect oligoribonucleotides (FIG. 2). A comparison of the one pot and two pot deprotection methods are outlined and demonstrated in FIG. 3.

This invention also concerns a rapid (high through-put) deprotection of RNA in a 96-well plate format. More specifically rapid deprotection of enzymatic RNA molecules in greater than microgram quantities with high biological activity is featured. It has been determined that the recovery of enzymatically active RNA in high yield and quantity is dependent upon certain critical steps used during its deprotection.

In a preferred embodiment, the invention features a process for one-pot deprotection of RNA molecules comprising protecting groups, comprising the steps of: a) contacting the RNA with a mixture of anhydrous alkylamine (where alkyl can be branched or unbranched, ethyl, propyl or butyl and is preferably methyl, e.g., methylamine), trialkylamine (where alkyl can be branched or unbranched, methyl, propyl or butyl and is preferably ethyl, e.g., ethylamine) and dimethylsulfoxide, preferably in a 10:3:13, or 1:0.3:1 proportion at temperature 20–30° C. for about 30–100 minutes, preferably 90 minutes, to remove the exocyclic amino (base) protecting groups and the phosphate protecting group (e.g., 2-cyanoethyl) (vs 4–20 h at 55–65° C. using $NH_4OH/EtOH$ or $NH_3/EtOH$, or 10–15 min at 65° C. using 40% aqueous methylamine) under conditions suitable for partial deprotection of the RNA; b) contacting the partially deprotected RNA with anhydrous triethylamine.hydrogen fluoride (3HF.TEA) and heating at about 50–70° C., preferably at 65° C., for about 5–30 min, preferably 15 min to remove the 2'-hydroxyl protecting group (vs 8–24 h using TBAF, or TEA.3HF for 24 h (Gasparutto et al. *Nucleic Acids Res.* 1992, 20, 5159–5166) (Other alkylamine.HF complexes may also be used, e.g. trimethylamine or diisopropylethylamine) under conditions suitable for the complete deprotection of the RNA. The reaction can then be quenched by using aqueous ammonium bicarbonate (1.4 M). Although some other buffers can be used to quench the desilylation reaction (i.e. triethylammonium bicarbonate, ammonium acetate), the ammonium bicarbonate buffer is perfectly suited to retain the 5'-O-dimethoxytrityl group at the 5'-end of the oligoribonucleotide thereby facilitating a reverse phase-based solid-phase extraction purification protocol.

By "one-pot" deprotection is meant that the process of deprotection RNA is carried out in one container instead of multiple containers as in two-pot deprotection.

In another preferred embodiment, the invention features a process for one pot deprotection of RNA molecules comprising protecting groups, comprising the steps of: a) contacting the RNA with a mixture of anhydrous alkylamine (where alkyl can be branched or unbranched, ethyl, propyl or butyl and is preferably methyl, e.g., methylamine), and dimethylsulfoxide, preferably in a 1:1 proportion at 20–30° C. temperature for about 30–100 minutes, preferably 90 minutes, to remove the exocyclic amino (base) protecting groups and the phosphate protecting group (e.g., 2-cyanoethyl) (vs 4–20 h at 55–65° C. using $NH_4OH/EtOH$ or $NH_3/EtOH$, or 10–15 min at 65° C. using 40% aqueous methylamine) under conditions suitable for partial deprotection of the RNA; b) contacting the partially deprotected RNA with anhydrous triethylamine.hydrogen fluoride (3HF.TEA) and heating at about 50–70° C., preferably at 65° C., for about 5–30 min, preferably 15 min to remove the 2'-hydroxyl protecting group (Other alkylamine.HF complexes may also be used, e.g. trimethylamine or diisopropylethylamine) under conditions suitable for the complete deprotection of the RNA. The reaction can then be quenched by using aqueous ammonium bicarbonate (1.4 M). Although some other buffers can be used to quench the desilylation reaction (i.e. triethylammonium bicarbonate, ammonium acetate), the ammonium bicarbonate buffer is perfectly suited to retain the 5'-O-dimethoxytrityl group at the 5'-end of the oligoribonucleotide thereby facilitating a reverse phase-based solid-phase extraction purification protocol.

In another aspect the invention features a process for RNA deprotection where the exocyclic amino and phosphate deprotection reaction is performed with the ethanolic methylamine solution at room temperature for about 90 min or at 65° C. for 15 min or at 45° C. for 30 min or at 35° C. for 60 min.

In a preferred embodiment, the process for deprotection of RNA of the present invention is used to deprotect a ribozyme synthesized using a column format as described in (Scaringe et al., supra; Wicott et al., supra).

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 shows the secondary structure model for seven different classes of enzymatic nucleic acid molecules. Arrow indicates the site of cleavage. --------- indicate the target sequence. Lines interspersed with dots are meant to indicate tertiary interactions. - is meant to indicate base-paired interaction. Group I Intron: P1–P9.0 represent various stem-loop structures (Cech et al., 1994, *Nature Struc. Bio.*, 1, 273). RNase P (M1RNA): EGS represents external guide sequence (Forster et al., 1990, *Science*, 249, 783; Pace et al., 1990, *J. Biol. Chem.*, 265, 3587). Group II Intron: 5'SS means 5' splice site; 3'SS means 3'-splice site; IBS means intron binding site; EBS means exon binding site (Pyle et al., 1994, *Biochemistry*, 33, 2716). VS RNA: I–VI are meant to indicate six stem-loop structures; shaded regions are meant to indicate tertiary interaction (Collins, International PCT Publication No. WO 96/19577). HDV Ribozyme: I–IV are meant to indicate four stem-loop structures (Been et al., U.S. Pat. No. 5,625,047). Hammerhead Ribozyme: I–III are meant to indicate three stem-loop structures; stems I–III can be of any length and may be symmetrical or asymmetrical (Usman et al., 1996, *Curr. Op. Struct. Bio.*, 1, 527). Hairpin Ribozyme: Helix 1, 4 and 5 can be of any length; Helix 2 is between 3 and 8 base-pairs long; Y is a pyrimidine; Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H refers to bases A, U, or C. Y refers to pyrimidine bases. "_" refers to a covalent bond. (Burke et al., 1996, *Nucleic Acids & Mol. Biol.*, 10, 129; Chowrira et al., U.S. Pat. No. 5,631,359).

FIG. 4 shows the results of a one-pot deprotection with different polar organic reagents.

SYNTHESIS AND PURIFICATION OF RNA

Figure 1A:
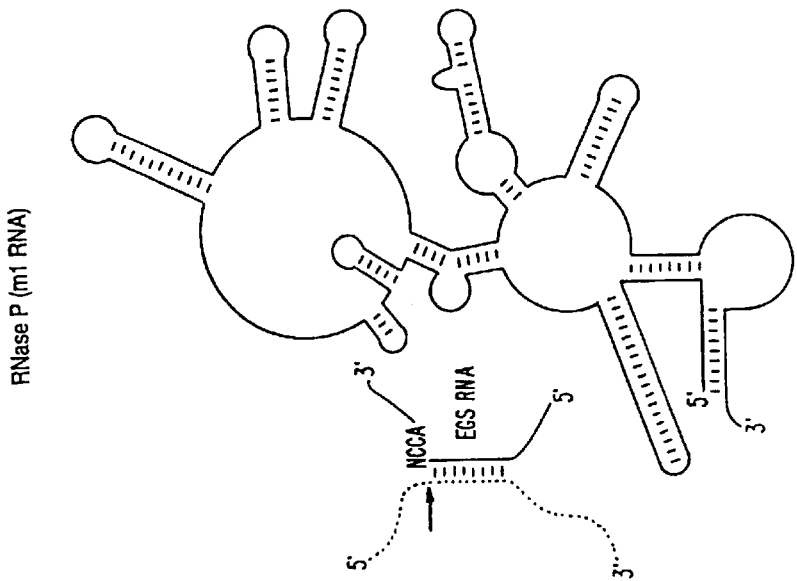
Figure 1A:
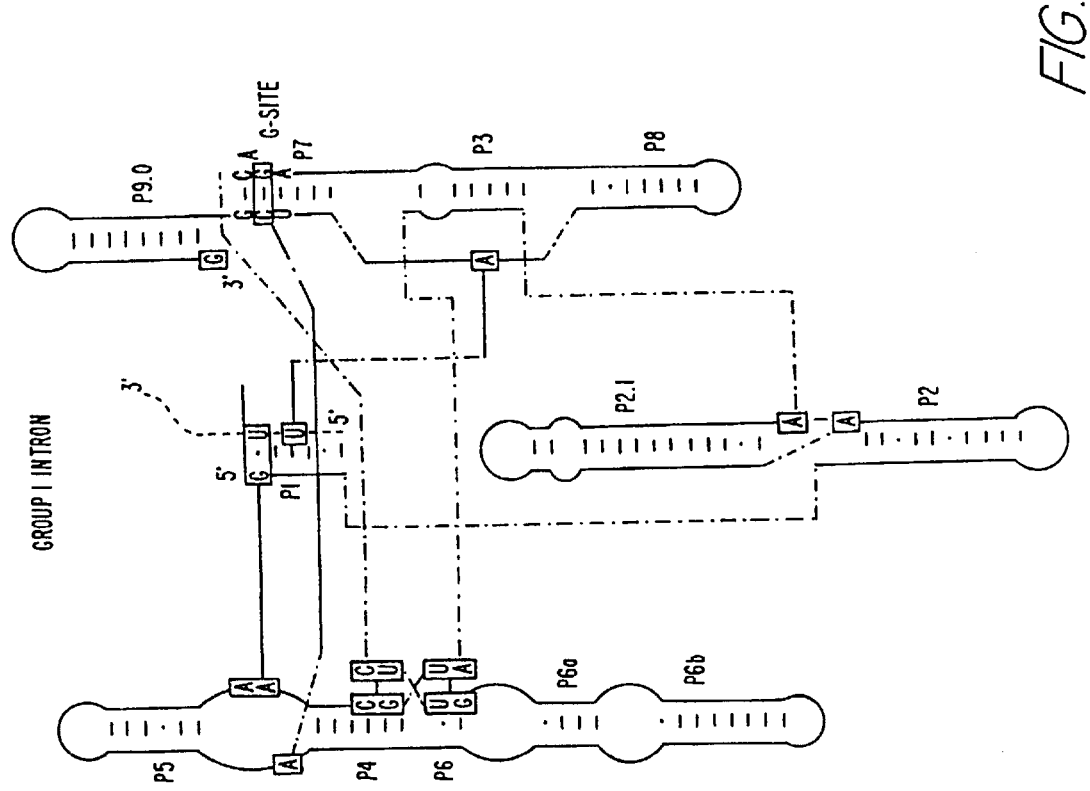
Figure 1B:
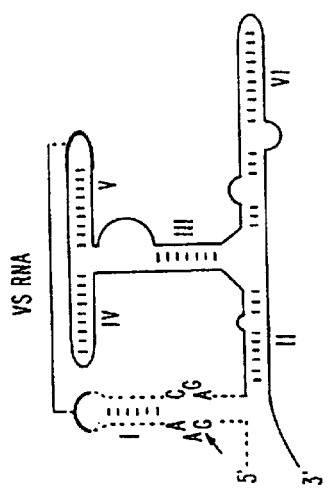
Figure 1B:
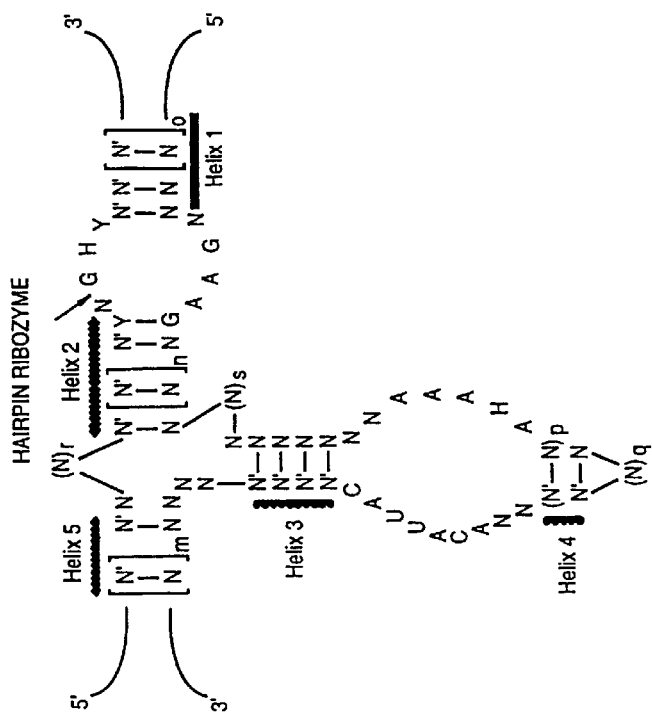
Figure 1B:
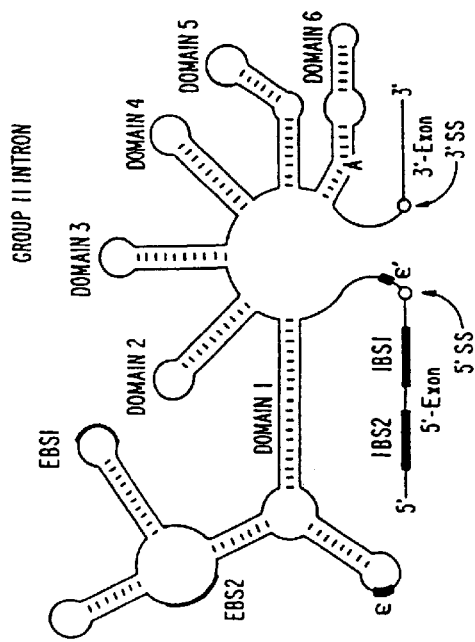
Figure 1B:
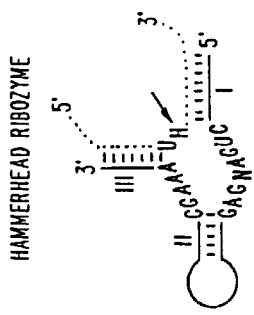
Figure 1B:
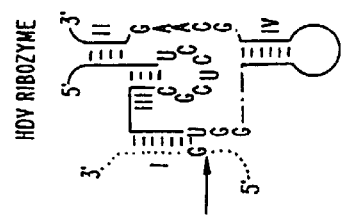

By "RNA" or "oligoribonucleotides" as used herein is meant a molecule having one or more ribonucleotides. The RNA can be single, double or multiple stranded and may comprise modified or unmodified nucleotides or non-nucleotides or various mixtures and combinations thereof.

RNA molecules can be chemically synthesized. The method of synthesis used follows the procedure for normal RNA synthesis as described in Usman et al., 1987 *J. Am.*

Chem. Soc., 109, 7845; Scaringe et al., 1990 Nucleic Acids Res., 18, 5433; and Wincott et al., 1995 Nucleic Acids Res. 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table I outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed according to the present invention. RNAs are purified by gel electrophoresis using general methods or are purified by high pressure liquid chromatography (HPLC; See Stinchcomb et al., International PCT Publication No. WO 95/23225, the totality of which is hereby incorporated herein by reference) and are resuspended in water.

Enzymatic RNA Molecules

The enzymatic RNA molecule is a nucleic acid molecule comprising at least one ribonucleotide. Enzymatic RNA molecule is able to intramolecularly or intermolecularly cleave RNA or DNA and thereby inactivate a target RNA or DNA molecule. The enzymatic RNA acid molecule that has complementarity in a substrate binding region to a specified gene target, also has an enzymatic activity that specifically cleaves RNA or DNA in that target. This complementarity functions to allow sufficient hybridization of the enzymatic RNA molecule to the target RNA or DNA to allow the cleavage to occur. 100% Complementarity is preferred, but complementarity as low as 50–75% may also be useful in this invention. The nucleic acids may be modified at the base, sugar, and/or phosphate groups.

The term enzymatic RNA acid is used interchangeably with phrases such as ribozymes, enzymatic nucleic acid, catalytic RNA, enzymatic RNA, nucleozyme, RNA enzyme, endoribonuclease, minizyme, leadzyme, oligozyme and the like.

By "complementarity" is meant a nucleic acid that can form hydrogen bond(s) with other RNA sequence by either traditional Watson-Crick or other non-traditional types (for example, Hoogsteen type) of base-paired interactions.

RNA molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, Nature 429 1986; Kim et al., 84 Proc. Natl. Acad. Sci. USA 8788, 1987; Haseloff and Gerlach, 334 Nature 585, 1988; Cech, 260 JAMA 3030, 1988; and Jefferies et al., 17 Nucleic Acids Research 1371, 1989).

Because of their sequence-specificity, trans-cleaving ribozymes show promise as therapeutic agents for human disease (Usman & McSwiggen, 1995 Ann. Rep. Med. Chem. 30, 285–294; Christoffersen and Marr, 1995 J. Med. Chem. 38, 2023–2037). Ribozymes can be designed to cleave specific RNA targets within the background of cellular RNA. Such a cleavage event renders the mRNA nonfunctional and abrogates protein expression from that RNA. In this manner, synthesis of a protein associated with a disease state can be selectively inhibited.

Seven basic varieties of naturally-occurring enzymatic RNAs are known presently. Each can catalyze the hydrolysis of RNA phosphodiester bonds in trans (and thus can cleave other RNA molecules) under physiological conditions. FIG. 1 summarizes some of the characteristics of these ribozymes. In general, enzymatic RNA act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

In one aspect enzymatic nucleic acid molecule is formed in a hammerhead or hairpin motif (FIG. 1), but may also be formed in the motif of a hepatitis delta virus (HDV), group I intron, RNaseP RNA (in association with an external guide sequence) or Neurospora VS RNA (FIG. 1). Examples of such hammerhead motifs are described by Rossi et al., 1992, Aids Research and Human Retroviruses 8, 183; Usman et al., 1996, Curr. Op. Struct. Biol, 1, 527; of hairpin motifs by Hampel et al., EP 0360257; Hampel and Tritz, 1989 Biochemistry 28, 4929; and Hampel et al., 1990 Nucleic Acids Res. 18, 299; Chowrira et al., U.S. Pat. No. 5,631,359; an example of the hepatitis delta virus motif is described by Perrotta and Been, 1992 Biochemistry 31, 16; Been et al., U.S. Pat. No. 5,625,047; of the RNaseP motif by Guerrier-Takada et al., 1983 Cell 35, 849; Forster and Altman, 1990 Science 249, 783; Neurospora VS RNA ribozyme motif is described by Collins (Saville and Collins, 1990 Cell 61, 685–696; Saville and Collins, 1991 Proc. Natl. Acad. Sci. USA 88, 8826–8830; Guo and Collins, 1995 EMBO J. 14, 368) and of the Group I intron by Zaug et al., 1986, Nature, 324, 429; Cech et al., U.S. Pat. No. 4,987,071. These specific motifs are not limiting in the invention and those skilled in the art will recognize that all that is important in an enzymatic nucleic acid molecule with endonuclease activity of this invention is that it has a specific substrate binding site which is complementary to one or more of the target gene RNA and that it have nucleotide sequences within or surrounding that substrate binding site which impart an RNA cleaving activity to the molecule. The length of the binding site varies for different ribozyme motifs, and a person skilled in the art will recognize that to achieve an optimal ribozyme activity the length of the binding arm should be of sufficient length to form a stable interaction with the target nucleic acid sequence.

Catalytic activity of the ribozymes described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 Nature 344, 565; Pieken et al., 1991 Science 253, 314; Usman and Cedergren, 1992 Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein).

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 TIBS 17, 34; Usman et al., 1994 Nucleic Acids Symp. Ser. 31, 163; Burgin et al., 1996 Biochemistry 35, 14090). Sugar modification of enzymatic nucleic acid molecules have been extensively described in the art (see Eckstein et al., International Publication PCT No. WO 92/07065; Perrault et al. Nature 1990, 344, 565–568; Pieken et al. Science 1991, 253, 314–317; Usman and Cedergren, Trends in Biochem. Sci. 1992, 17, 334–339; Usman et al. International Publication PCT No. WO 93/15187; Sproat, U.S. Pat. No. 5,334,711 and Beigelman et al., 1995 J. Biol. Chem. 270, 25702; all of the references are hereby incorporated in their totality by reference herein).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

Nucleic acid catalysts having chemical modifications which maintain or enhance enzymatic activity are provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, Biochemistry, 35, 14090). Such ribozymes herein are said to "maintain" the enzymatic activity on all RNA ribozyme.

By "nucleotide" as used herein is as recognized in the art to include natural bases (standard), and modified bases well known in the art. Such bases are generally located at the 1' position of a sugar moiety. Nucleotide generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art and has recently been summarized by Limbach et al., 1994, Nucleic Acids Res. 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, Biochemistry, 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

By "unmodified nucleoside" is meant one of the bases adenine, cytosine, guanine, uracil joined to the 1' carbon of β-D-ribo-furanose.

By "modified nucleoside" is meant any nucleotide base which contains a modification in the chemical structure of an unmodified nucleotide base, sugar and/or phosphate.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Deprotection of RNA

For high throughput chemical synthesis of oligoribonucleotides, it is important that the two main steps involved in the deprotection of oligoribonucleotides (i.e. aqueous basic treatment to remove exocyclic amino protecting groups and phosphate protecting groups and fluoride treatment to remove the 2'-OH alkylsilyl protecting groups such as the tButylDiMethylSilyl) are condensed.

Figure 3:
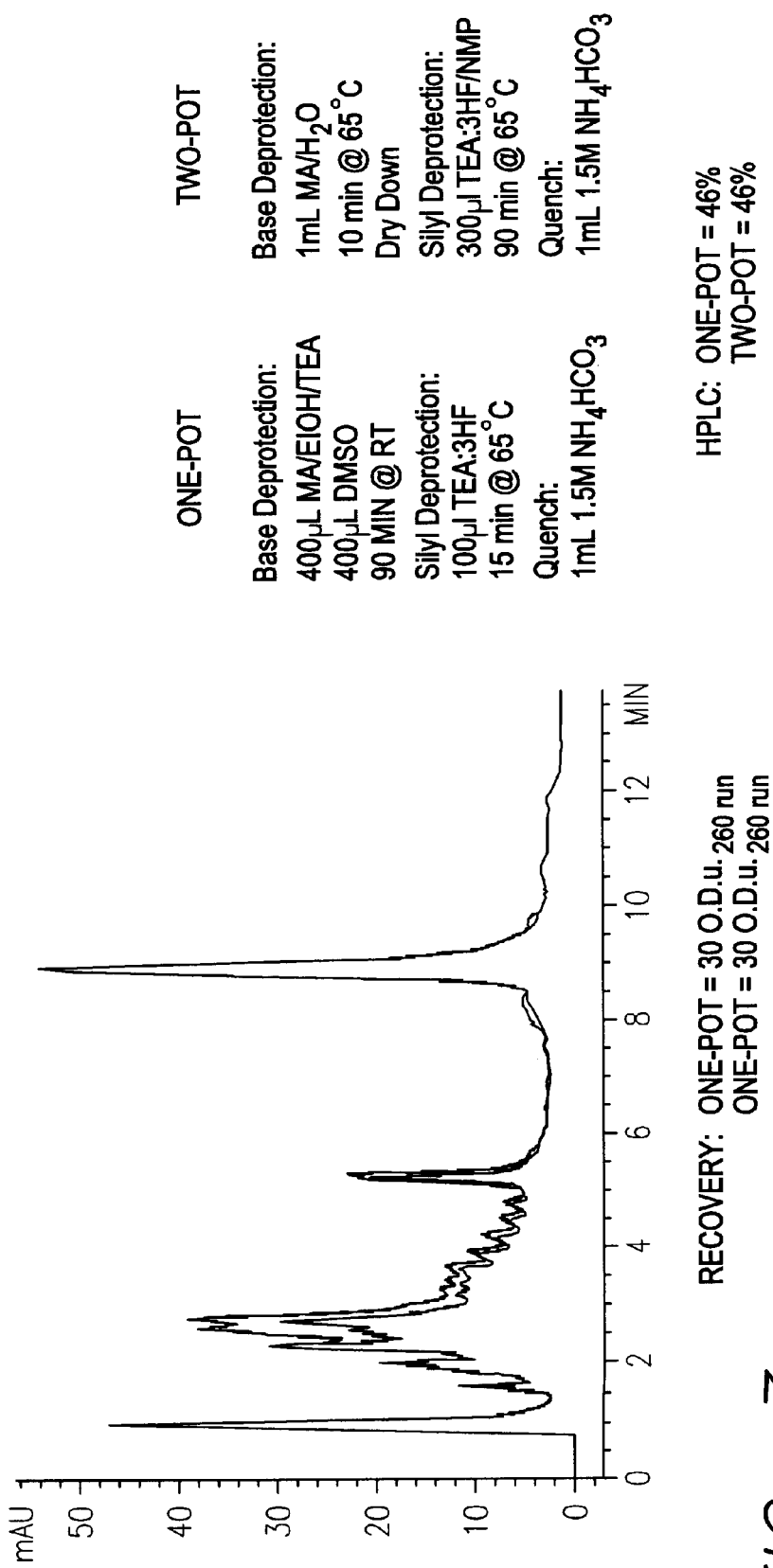
FIG. 3 is a comparison of a one-pot and a two-pot process for deprotection of RNA.

Stinchcomb et al., supra describe a time-efficient (~2 hrs) one-pot deprotection protocol based on anhydrous methylamine and triethylamine trihydrogen fluoride. Since it has recently been reported that water contamination during fluoride treatment may be detrimental to the efficiency of the desilylation reaction (Hogrefe et al, Nucleic Acids Res. (1993), 21 4739–4741), it is necessary to use an anhydrous solution of base such as a 33% methylamine in absolute ethanol followed by neat triethylamine trihydrofluoride to effectively deprotect oligoribonucleotides in a one-pot fashion. However it may be cumbersome to apply such a protocol to plate format deprotection where the solid-support is preferentially separated from the partially deprotected oligoribonucleotides prior to the 2'-hydroxyl deprotection. Indeed, because the methylamine solution used is anhydrous, it may not be suitable to solubilize the negatively charged oligoribonucleotides obtained after basic treatment. Therefore, applicant investigated a 1:1 mixture of the ethanolic methylamine solution and different polar additives such as dimethylsulfoxide (DMSO), N,N-dimethylformamide (DMF), methanol, hexamethylphosphoramide (HMPA), 1-methyl-2-pyrrolidinone (NMP) or 2-methoxyethyl ether (glyme). Of all these additives, dimethylsufoxide is capable of efficiently solubilizing partially deprotected oligoribonucleotides (FIG. 4). A comparison of the one pot and two pot deprotection methods are outlined and demonstrated in FIG. 3.

EXAMPLES

The following are non-limiting examples showing the deprotection of RNA.

Example 1
Deprotection of Ribozyme in a 96 Well Plate

Figure 2:
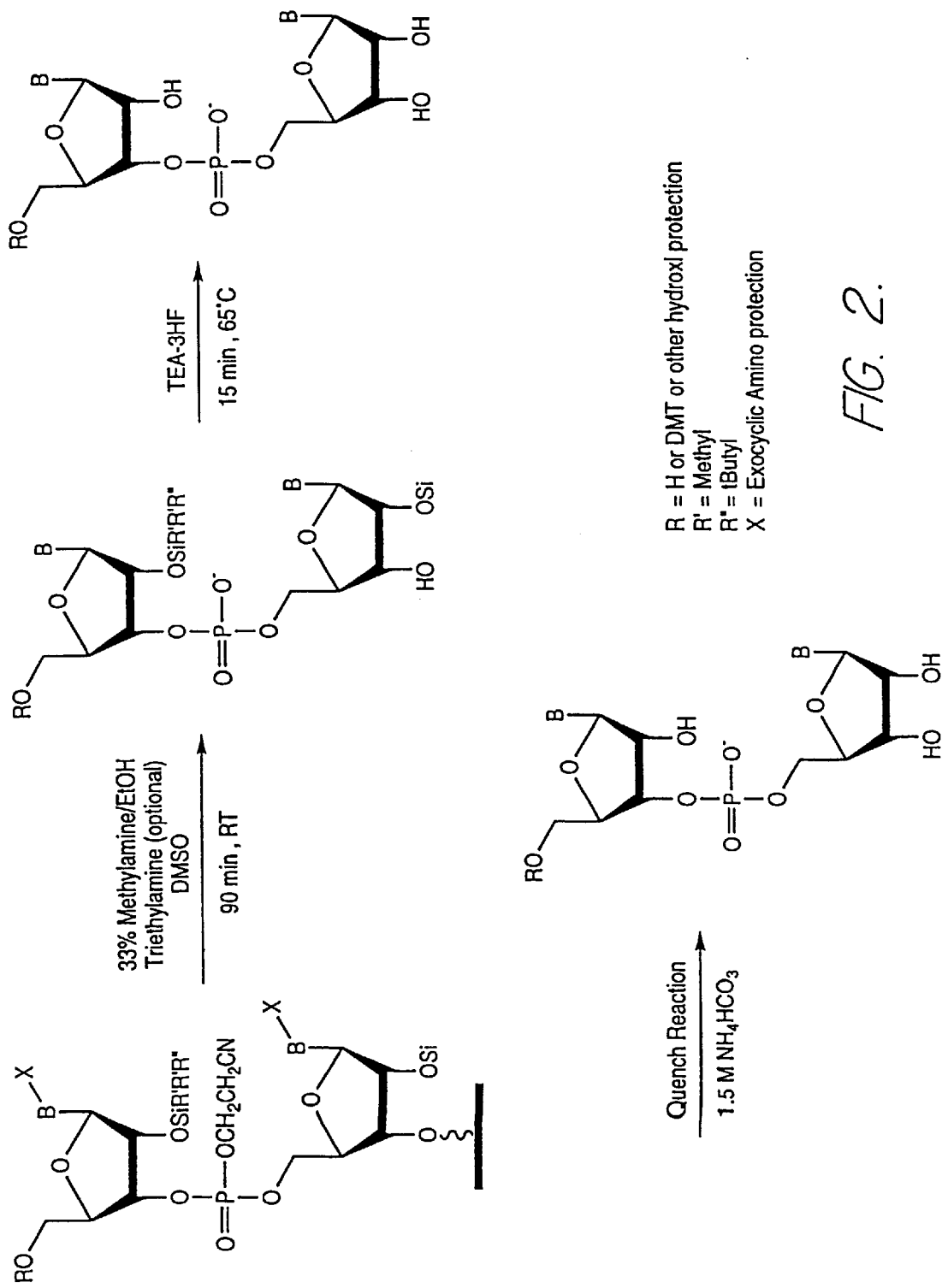
FIG. 2 is a is a schematic representation of a one pot deprotection of RNA synthesized using RNA phosphoramidite chemistry.

A ribozyme sequence (200nmole) was synthesized as described herein on a polystyrene solid support in a well of a 96 well plate. A 10:3:13 mixture (800 µL) of anhydrous methylamine (308 µL), triethylamine (92 µL) and dimethylsulfoxide (DMSO) (400 µL) was prepared of which half (400 µL) was added to the well and incubated at room temperature for 45 minutes. Following the reaction the solution was replaced with the remaining 400 µL and incubated as before. At the end of the reaction, the solid support was filtered off, all 800 µL of MA/TEA/DMSO solution was collected together and 100 µL of TEA.3HF was added. The reaction was then heated at 65° C. for 15 minutes and then cooled to room temperature. The solution was then quenched with aqueous $NH_4^+HCO_3^-$ (1 mL) (see FIG. 2). HPLC chromatography of the reaction mixture afforded 32 O. D.$u_{260\ nm}$ of which 46% was full length ribozyme.

Example 2
Column Deprotection of Ribozyme

A ribozyme was synthesized using the column format as described herein. The polystyrene solid-support with protected oligoribonucleotide or modified oligoribonucleotide (200 nmole) was transferred into a glass vial equipped with a screw cap. A 10:3:13 mixture of anhydrous methylamine (308 µL), triethylamine (92 µL) and dimethylsulfoxide (DMSO) (400 µL) was added followed by vortexing of the glass vial. After allowing the reaction for 1.5 hours, the solid support was filtered off. 100 µL of TEA.3HF was added at room temperature to the vial and the reaction was mixed causing the solution to gel. The reaction was then heated at 65° C. for 15 minutes and then cooled to room temperature. The solution was then quenched with 1.5 M aqueous $NH_4^+$ $HCO_3^-$ (1 mL). HPLC chromatography of the reaction mixture afforded 32 O. D.$u_{260\ nm}$ of which 46% was full length ribozyme.

Example 3
Column Deprotection of Ribozyme with Anhydrous Ethanolic Methylamine

A ribozyme was synthesized using the column format as described herein. The polystyrene solid-support with protected oligoribonucleotide or modified oligoribonucleotide (200 nmole) was transferred into a glass vial equipped with a screw cap. A 1:1 mixture of anhydrous ethanolic methylamine (400 µL) and dimethylsulfoxide (DMSO) (400 µL) was added followed by vortexing of the glass vial. After allowing the reaction for 1.5 hours, the solid support was filtered off. 100 µL of TEA.3HF was added at room temperature to the vial and the reaction was mixed causing the solution to gel. The reaction was then heated at 65° C. for 15 minutes and then cooled to room temperature. The solution was then quenched with 1.5 M aqueous $NH_4^+HCO_3^-$ (1 mL). HPLC chromatography of the reaction mixture afforded 32 O. D.$u_{260\ nm}$ of which 46% was full length ribozyme.

Example 4

Large-scale One-Pot Deprotection of Ribozyme

A ribozyme was synthesized at the 0.5 mmol scale using the column format as described herein. The polystyrene solid-support (24 grs) with protected oligoribonucleotide or modified oligoribonucleotide (500 µmole) was transferred into a 1 L Schott bottle equipped with a screw cap. A 1:1.3 mixture of anhydrous ethanolic methylamine (150 mnL) and dimethylsulfoxide (DMSO) (200 mL) was added followed by vortexing (200 rpm) of the glass bottle for 1.5 hours. The reaction mixture was then frozen at −70° C. for 30 minutes. 50 mL of neat TEA.3HF was then added at room temperature to the reaction mixture and the reaction was placed in a shaking oven (200 rpm) where it was heated at 65° C. for 60 minutes and subsequently frozen at −70° C. for 30 minutes. The solution was then quenched with 1.5 M aqueous $NH_4^+HCO_3^-$ (200 mL). The reaction mixture was separated from the polystyrene solid-support by filtration on a sintered glass funnel (10–20 µm porosity). U.V. spectrophotometric quantification and HPLC chromatography of the reaction mixture afforded 160,000 O.D.$u_{260\ nm}$ of which 46.4% was full length ribozyme. After allowing the reaction for 1.5 hours, the solid support was filtered off.

Other embodiments are within the following claims.

TABLE I 2.5 µmol RNA Synthesis Cycle

| Reagent | Equivalents | Amount | Wait Time* |
|---|---|---|---|
| Phosphoramidites | 6.5 | 163 µL | 2.5 |
| S-Ethyl Tetrazole | 23.8 | 238 µL | 2.5 |
| Acetic Anhydride | 100 | 233 µL | 5 sec |
| N-Methyl Imidazole | 186 | 233 µL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

What is claimed is:

1. A process for one pot deprotection of RNA synthesized on the surface of a well in a plate having a defined number of wells, comprising the steps of:
   a) contacting said RNA with a mixture of anhydrous alkylamine, trialkylamine and a polar organic reagent in a predetermined proportions, at room temperature for about between 30 and 100 min under conditions suitable for the removal of nucleic acid base and phosphate protecting groups from said RNA; and
   b) contacting said base and phosphate deprotected RNA with a anhydrous triethylamine.hydrogen fluoride at about between 50° C.–70° C. under conditions suitable for the removal of 2'-OH protecting group.

2. The process of claim 1 wherein said RNA is an enzymatic RNA molecule.

3. The process of claim 2, wherein said enzymatic RNA molecule is in a hammerhead motif.

4. The process of claim 1, wherein said polar organic reagent is dimethylsulfoxide.

5. The process of claim 1, wherein said anhydrous alkylamine is anhydrous methyl amine.

6. The process of claim 1, wherein said anhydrous alkylamine is anhydrous ethylamine.

7. The process of claim 1, wherein said trialkylamine is triethylamine.

8. The process of claim 4, wherein the predetermined proportion of anhydrous alkylamine, trialkylamine and dimethylsulfoxide in said mixture is 10, 3 and 13, respectively.

9. The process of claim 1, wherein said plate has 96 wells.

10. A process for one pot deprotection of RNA synthesized on the surface of a well in a plate having a defined number of wells, comprising the steps of:
   a) contacting said RNA with a mixture of anhydrous methylamine, triethylamine and dimethylsulfoxide in proportions of 10, 3 and 13, respectively, at room temperature for about 90 min under conditions suitable for the removal of nucleic acid base and phosphate protecting groups from said RNA; and
   b) contacting said base and phosphate deprotected RNA with a anhydrous triethylamine.hydrogen fluoride at about between 65° C. under conditions suitable for the removal of 2'-OH protecting group.

11. The process of claim 10, wherein said RNA is an enzymatic RNA molecule.

12. The process of claim 11, wherein said enzymatic RNA molecule is in a hammerhead motif.

13. The process of claim 10, wherein said plate has 96 wells.

14. The process of claims 1 or 10, wherein said RNA comprises at least one sugar modification.

15. The process of claim 1 or 10, wherein said RNA comprises at least one phosphate backbone modification.

16. The process of claim 1 or 10, wherein said RNA comprises at least one nucleotide base modification.

17. The process of claim 14, wherein said sugar modification is selected from the group consisting of 2'-O-methyl, 2'-H, 2'-C-allyl, 2'-fluoro and 2'-amino.

18. The process of claim 14, wherein said phosphate backbone modification is phosphorothioate.

19. The process of claims 1 or 10, wherein the sequence of the RNA synthesized in each said defined number of wells is different.

* * * * *